United States Patent
Cragoe, Jr. et al.

[11] 3,953,476
[45] Apr. 27, 1976

[54] 3-AMINO-5-SULFONYLBENZOIC ACIDS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[22] Filed: May 1, 1974

[21] Appl. No.: 465,949

Related U.S. Application Data

[60] Continuation of Ser. No. 212,745, Dec. 27, 1971, abandoned, which is a division of Ser. No. 33,061, April 29, 1970, Pat. No. 3,780,027.

[52] U.S. Cl. ............... 260/347.2; 260/247.1 R; 260/247.1 S; 260/247.1 P; 260/268 C; 260/293.67; 260/293.68; 260/293.73; 260/294.8 R; 260/332.2 A; 260/326.5 E; 260/470; 260/518 R; 260/518 A; 260/519; 260/558 S; 424/275; 424/284; 424/310; 424/317

[51] Int. Cl.² ............................. C07D 307/52

[58] Field of Search ............ 260/347.2, 518, 519, 260/470, 332.2

[56] References Cited
UNITED STATES PATENTS

3,250,764  5/1966  Schmidt et al. ............... 260/239.8
3,560,617  2/1971  Feit et al. ............... 260/578
3,678,039  7/1972  Werner et al. ............... 260/397.7

OTHER PUBLICATIONS

Feit et al. II, Chem. Abst., Vol. 71, Item 3141y, (7/7/69), (Abstract of So. African Patent 68/03145, Publ. 21 Oct. 1968).

*Primary Examiner*—Harry I. Moatz
*Attorney, Agent, or Firm*—David L. Rose; J. Jerome Behan

[57] ABSTRACT

Aminobenzoic acids of the structure

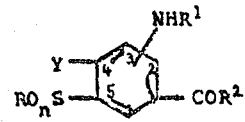

having saluretic and diuretic properties are described. These compounds are prepared by amidation of a 2-halo analog thereof or by alkylation of the free amino compound.

6 Claims, No Drawings

3-AMINO-5-SULFONYLBENZOIC ACIDS

This is a continuation of application Ser. No. 212,745 filed Dec. 27, 1971, now abandoned, which is a division of application Ser. No. 33,061 filed Apr. 29, 1970, now U.S. Pat. No. 3,780,027 issued Dec. 18, 1973.

This invention is concerned with 2-(or 3-)-amino-4-substituted-5-sulfonyl (or sulfinyl)-benzoic acids and derivatives thereof and to methods by which these novel compounds can be prepared.

The novel compounds of this invention can be illustrated by the following structure, III,

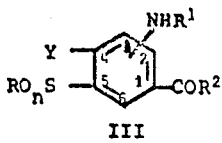

III wherein
Y represents
1. halogen such as chloro, bromo, fluoro but particularly chloro,
2. trifluoromethyl, and
3. $C_{1-3}$ alkyl, R represents
1. lower alkyl particularly having from 1 to 5 carbon atoms,
2. halo-lower alkyl (e.g., $C_{1-5}$) particularly fluoro-lower alkyl and chloro-lower alkyl,
3. phenyl-lower alkyl ($C_{1-3}$) wherein the phenyl moiety is either unsubstituted or substituted with one or more groups selected from lower alkyl, lower alkoxy, or halo;

$n$ is the numeral 1 or 2;

—$NHR^1$ is attached to the 2- or 3-position nuclear carbon and the variable radical $R^1$ is selected from
1. lower alkyl having from 1 to 5 carbon atoms,
2. substituted lower alkyl having from 1 to 3 carbon atoms, and wherein the substituent group is selected from
   a. phenyl or substituted phenyl wherein the substituent(s) is(are) selected from one or more halogen atoms particularly chlorine and fluorine, a trifluoromethyl, lower alkyl having from 1 to 3 carbon atoms or lower alkoxy having from 1 to 3 carbon atoms,
   b. naphthyl,
   c. a 5- or 6-membered heterocycle having oxygen, sulfur or nitrogen as a hetero atom such as pyridyl, furyl, a carboxy substituted furyl, tetrahydrofuryl, thenyl, and the like,
   d. halo, particularly fluoro and chloro,
   e. hydroxy,
   f. di-loweralkylamino wherein each alkyl substituent has from 1 to 3 carbon atoms,
   g. lower cycloalkyl wherein the cycloalkyl moiety has from 3 to 6 carbons and wherein the cycloalkyl moiety can be substituted advantageously with an hydroxy-lower alkyl ($C_{1-3}$) group,
3. cycloalkyl advantageously having from 3 to 6 carbon atoms,
4. phenyl or substituted phenyl wherein the substituents can be one or more radicals selected from halogen, trifluoromethyl, lower alkyl and lower alkoxy, the alkyl moieties having advantageously from 1 to 3 carbon atoms; and
5. amino or mono- or di-lower alkyl($C_{1-3}$)amino;

$R^2$ represents
1. hydroxy, OH, or its pharmaceutically acceptable salts particularly the sodium, potassium, calcium, ammonium and the like salts,
2. $OR^3$ wherein $R^3$ is selected from lower alkyl ($C_{1-5}$) and di-loweralkyl($C_{1-3}$)aminoloweralkyl($C_{1-3}$), and
3. —$NR^4R^5$ wherein $R^4$ is selected from
   a. hydrogen,
   b. $C_{1-3}$ alkyl,
   c. amino,
   d. di-loweralkylamino,
   e. guanidino,
   f. amidino,
   g. di-loweralkyl($C_{1-3}$)amino-loweralkyl($C_{1-3}$),
   h. morpholino-lower alkyl,
$R^5$ is selected from hydrogen and loweralkyl($C_{1-3}$), and
$R^4$ and $R^5$ can be joined to form a 5- or 6-membered cyclic structure with the nitrogen atom to which they are attached to form, for example, a 1-pyrrolidinyl, piperidino, morpholino, 4-loweralkylpiperazinyl and the like.

The novel compounds of this invention can readily be prepared by one or another of the reactions illustrated in Reaction Scheme I:

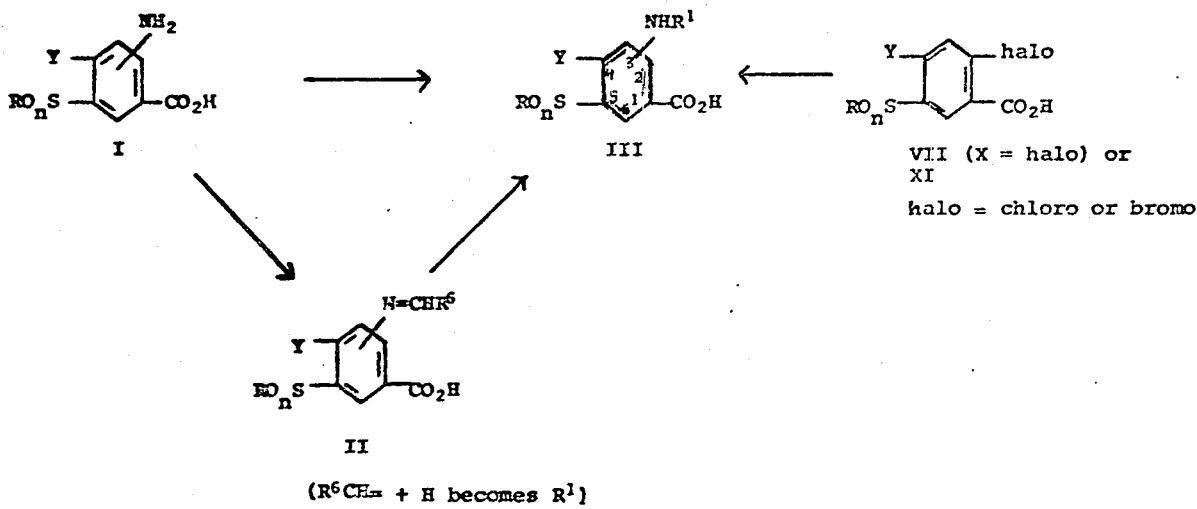

The benzoic acid compound III of this invention can be made by one of various routes. The most direct involves the alkylation of the benzoic acid compound I which advantageously can be carried out using an alkylating agent such as $R^1$—halide, $R^1$—$OSO_3$—$R^1$, $R^1OSO_2$—$C_6H_5$, $R^1$—$OSO_2$—alkyl, and the like. The reaction preferably is conducted in an inert solvent such as water, alkanols, dimethylformamide, mixtures of these solvents or indeed any other inert solvent. The reaction can, if desired, be conducted in the presence of a substance which reacts with the hydrohalide that is generated. This substance may be a base such as an alkali metal bicarbonate, carbonate or hydroxide. Temperatures from ambient to reflux temperature can be employed and the time required to achieve maximum yields generally is dependent upon the temperature and can vary from several hours to a day or more.

Alternatively, the benzoic acid compound I can be converted to the corresponding Schiff's base, II, which upon reduction provides the product III. The reaction of the benzoic acid compound I with the aldehyde $R^6CHO$ can be carried out either with or without a solvent. Excess aldehyde can be employed as the solvent or inert solvents such as acetic acid, alkanols, and the like can be employed if desired. Temperatures ranging between ambient to about 70° C. or higher can be employed and the reaction can be facilitated by removing the water that is generated by distillation at atmospheric or reduced pressures. The intermediate Schiff's base, II, can be isolated before reduction or it can be reduced in situ. The reduction can be carried out using conventional reducing agents such as alkali borohydrides, trialkylamine borane complexes, or by catalytic hydrogenation. The alkali borohydride preferably are conducted at ambient temperatures or slightly above or below and advantageously in a solvent such as an alkanol or water. The tri-alkylamine borane complex reductions generally are carried out in the presence of an inert solvent such as dioxane or acetic acid while catalytic hydrogenation generally is carried out at ambient temperature in the presence of an inert solvent such as tetrahydrofurane, dioxane, acetic acid or alkanols. Catalysts which are particularly suitable for this reduction are Raney nickel or palladium supported on carbon.

Additionally, the products of this invention, III, can be prepared from a 2-halo-4-Y-5-$RO_nS$-benzoic acid, VII, (X = halo) or XI, (see Reaction Scheme II) by reaction with the selected amine, $R^1NH_2$. The starting substances advantageously are heated to a temperature between about 120°–180° C. and, if necessary, in the presence of an inert organic solvent or diluent it being of advantage to choose a two to four times excessive amount of the basic reactant in order to bind the hydrogen halide set free in the reaction. The reaction temperature depends, to a marked degree, upon the type of amine used. Instead of using an excess of the amine in order to bind the hydrogen halide set free in the course of the reaction, other usual basic agents can be employed. Certain especially suitable basic agents would be alkali metal bicarbonates, calcium oxide, or tertiary organic bases such as triethylamine, 1,5-diazabicyclo[4.3.0]non-5-ene and the like. It has been found that even though the reaction is carried out in the temperature range between about 120° and 180° C. that a halogen atom in the 4-position does not participate in the reaction even when large amounts of the amine reactant is employed.

The reaction can be carried out by fusing the reactants or, if desired, a solvent or diluent, for example water or inert solvents miscible with water such as an alkanol, ethylene-glycol, ethylene-glycol-monomethylether, diethylene-glycol-dimethylether, and the like can be employed. Depending upon the type of starting materials used, the reaction mixture can be heated for shorter or longer periods under reflux, or if necessary in a closed vessel. The reaction generally is completed within one to four hours although under certain circumstances it can be prolonged up to 12 to 24 hours particularly when operating at low temperatures in order to avoid side reactions.

The esters, amides and salts of product III can be prepared by conventional methods. The alkyl esters of the benzoic acids of this invention are prepared by conventional methods such as by the reaction of the benzoic acid III with an alkanol using a catalyst such as sulfuric acid or boron trifluoride. Esters derived from alcohols of the type HO—$C(R^7)$=CH—CONH-alkyl are prepared by known procedures from the appropriate N-alkylisoxazolium salt having the structural formula

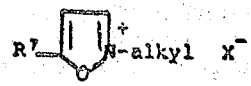

where $R^7$ is lower alkyl, phenyl or substituted phenyl, especially a sulfophenyl, and the like and X is the anion of a salt forming compound. The enol esters thus formed are especially useful in preparing derivatives such as products having the general structural formula

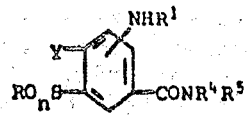

by reaction of the said ester with the appropriate amine, $HNR^4R^5$. The amide derivatives can additionally be prepared from the alkyl esters of III by reaction with the amine, $HNR^4R^5$.

Salts of the novel benzoic acids, III are obtained by treatment with mineral or organic bases such as, for example, ammonia, alkali metal or alkaline earth metal carbonates, alkali metal or alkaline earth metal bicarbonates, alkali metal or alkaline earth metal hydroxides, alkali metal or alkaline earth metal oxides or by reaction with an organic base.

The starting materials, I, VII and XI employed to prepare the novel products, III, of this invention can be synthesized by methods illustrated below in Reaction Scheme II.

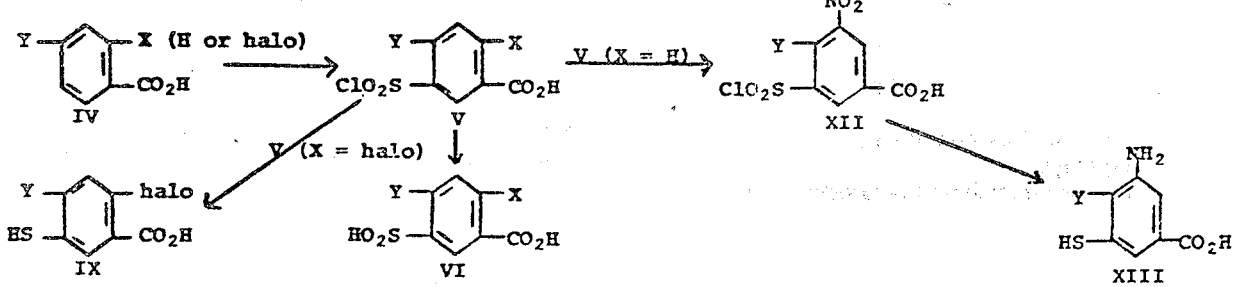

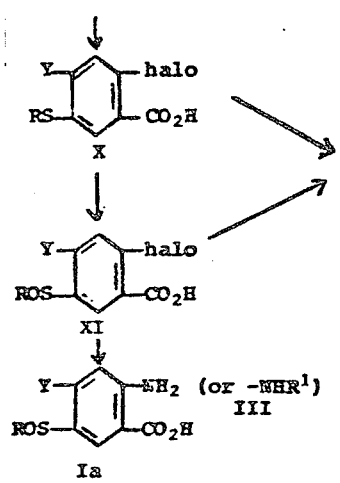
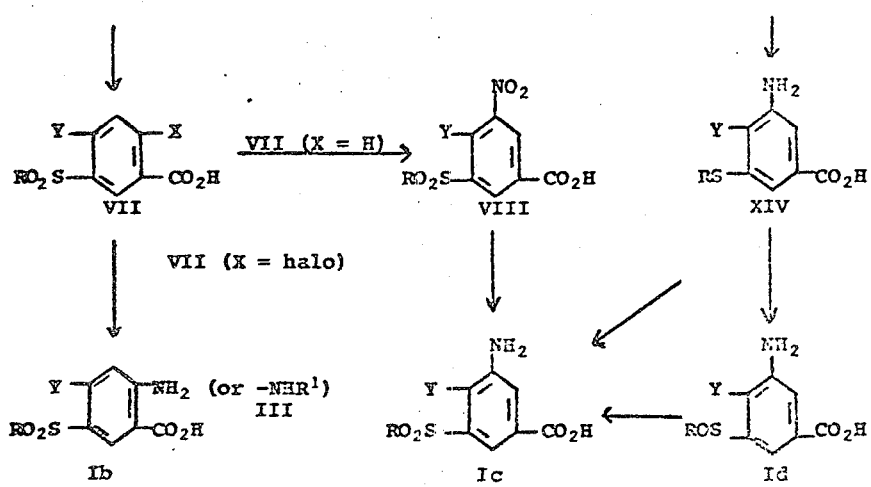

All of the starting materials, Ia, to Id, can be prepared from the 4-Y-benzoic acid, IV. The starting substance, Ib, is prepared by first chlorosulfonating the benzoic acid compound IV advantageously using chlorosulfonic acid as the chlorosulfonating agent and preferably using an excess of the acid for its solvent properties. The optimum temperature generally is in the range of 130° C. to reflux although temperatures substantially lower can be employed depending upon the nature of the starting material.

The sulfinic acid, VI, is prepared by reduction of the sulfonyl chloride, V, by any one of several procedures. Sodium bisulfite has been found especially effective for this reduction.

Alkylation of a salt of the sulfinic acid, VI, effected by the usual alkylating agents (such as alkyl- or aralkyl halides, -sulfates, and the like) provides the sulfone compound, VII. The sulfone compound, VII, also can be prepared by oxidation of the sulfoxide, XI, by employing an excess of the same oxidizing agent used in converting the thio ethers, X, to the sulfoxides, XI, or by employing another known oxidizing agent.

The starting material, Ib, is prepared from compound VII (X = halo) by reaction with ammonia. As mentioned previously, the compound VII (X = halo) can be converted directly to the products of this invention, III, by reaction with the selected amine, $R^1NH_2$. In the preparation of Ib, it has been found that pure ammonia or solutions of ammonia in an inert solvent can be used and the reaction conducted preferably in a closed vessel at temperatures generally in the range of 150°–190° C.

The sulfoxide starting material, Ia, is prepared from the benzoic acid, IV, by first chlorosulfonating as described above to produce compound V. The sulfonyl chloride compound, V, is reduced by any one of several reducing agents, although stannous chloride has been found to be especially useful for this purpose thus forming the 5-mercaptobenzoic acid, IX.

The mercaptobenzoic acid, IX, then is reacted with an alkylating or aralkylating agent (which can be the same as those employed for the alkylation of compound VI) to form compound, X.

Oxidation of thio ether, X, by any one of a large variety of oxidizing agents, and in most instances employing stoichiometric amounts of the oxidizing agent, provides the desired sulfoxide compound, XI. Further oxidation of this compound as mentioned above, provides the sulfone, VII. Particularly useful oxidizing agents are hydrogen peroxide, peracids or their salts, for example, m-chloroperbenzoic acid, sodium periodate, nitric acid, chromic oxide, potassium permanganate as well as other conventional oxidizing agents.

Compound XI can be reacted with ammonia to give starting material Ia or with an amine, $R^1NH_2$, to provide a product of this invention, III, by the methods discussed above.

The 3-aminobenzoic acid compounds of this invention are prepared in the following manner.

The 3-aminobenzoic acid compounds having in the 5-position the substituent $RO_2S$—, starting materials Ic, advantageously are prepared from the benzoic acid compound, VII (X = H), by nitration to provide the 3-nitro analog, VIII, by well known nitration procedures such as by using concentrated sulfuric acid and concentrated nitric acid at temperatures in the range of 70°–100° C.

The 3-nitro compound, VIII, then is reduced to the corresponding 3-amino compund, Ic, by any one of several well known procedures; an especially useful method employs iron and hydrochloric acid in aqueous media.

The 3-aminobenzoic acids having a sulfoxide, ROS—, substituent in the 5-position, Id, are prepared from the chlorosulfonated benzoic acid compound V (X = H) by nitration by well known methods such as by using concentrated sulfuric acid and nitric acid at temperatures in the range of 70°–100° C. to provide compound XII.

The nitro compound XII then is reduced to the 3-amino-5-mercaptobenzoic acid XIII by any one of several well known procedures; particularly by employing stannous chloride and hydrochloric acid in aqueous media by methods previously discussed. This compound, XIII, then is alkylated to form compound XIV by the same procedure described for the alkylation of compound VI to give compound VII.

Oxidation of the thio ether, XIV, by a variety of oxidizing agents employing a stoichiometric amount of the oxidizing agent provides starting material Id. Employing an excess of oxidizing agent will give the sulfone starting material Ic. The oxidizing agents and procedures are the same as those discussed above in relation to the oxidation of compound X to give either compound XI or VII.

The new products of this invention exhibit diuretic and saluretic properties and thus are useful agents for the treatment of edema and hypertension when administered as the sole active agent or when administered along with, either separately or in a combination dosage form, with other active agents having diuretic, antihypertensive or other therapeutic properties. The products of this invention have not produced gross toxic manifestations at effective dose levels and are active in their free form as well as in the form of their salts upon oral as well as parenteral administration. Pharmaceutical formulations of these products can be prepared by conventional methods either in solid or liquid form. Dosages ranging between about 0.01 gram to about 0.3 grams of the active product for administration on a 1 to 4 times a day regimen can be prepared for the symptomatic adjustment of the dose to be recommended by the physician or veterinarian.

All melting points given in the following examples are corrected values.

EXAMPLE 1

2-Furfurylamino-4-chloro-5-methylsulfonylbenzoic acid

Step A: Preparation of 2,4-dichloro-5-carboxybenzenesulfinic acid.

A three liter flask equipped with a mechanical stirrer, thermometer and dropping funnel is charged with sodium sulfite (378 g.; 3.0 moles) and water (1 liter). The solution is cooled in an ice bath and treated with 2,4-dichloro-5-chlorosulfonylbenzoic acid (290 g.; 1.0 mole) and 10N sodium hydroxide (290 ml.) simultaneously in small portions over a period of 1.5 hours keeping the temperature below 20° C. and the pH of the reaction at 9. When the addition of the reagents is complete, the reaction is stirred for 3 hours at 25° C. then cooled to 10° C. and acidified with concentrated hydrochloric acid (440 ml.). The 2,4-dichloro-5-carboxybenzenesulfinic acid which precipitates is filtered, washed with ice water, then used in the next step without further purification.

Step B: Preparation of 2,4-dichloro-5-methylsulfonylbenzoic acid

The product of Step A is placed in a three-liter flask to which is added water (300 ml.), methanol (500 ml.) sufficient 10N sodium hydroxide to attain a pH of 9 and methyl iodide (520 g.; 3.66 moles). The reaction mixture is refluxed for 36 hours with the occasional addition of 10N sodium hydroxide to maintain pH 9. The alcohol is distilled at reduced pressure and the reaction solution is acidified with hydrochloric acid. The product is filtered, washed with water, dried and recrystallized from ethanol (800 ml.) to give 150 g. (yield 56%) 2,4-dichloro-5-methylsulfonylbenzoic acid, m.p. 210°–211° C.

Analysis calculated for $C_8H_8Cl_2O_4S$: C, 35.70; H, 2.25; Cl, 26.35; Found: C. 35.61; H, 2.34; Cl, 26.27.

Step C: Preparation of 2-furfurylamino-4-chloro-5-methylsulfonylbenzoic acid

A mixture of 2,4-dichloro-5-methylsulfonylbenzoic acid (15 g.; 0.055 mole) and furfurylamine (30 ml.) is heated in an oil bath at 125° C. under an atmosphere of nitrogen for 3 hours then poured into cold, dilute hydrochloric acid (200 ml.) to precipitate 17.6 g., (98%) of 2-furfurylamino-4-chloro-5-methylsulfonylbenzoic acid, m.p. 204° C. (dec.) after recrystallization from nitromethane (200 ml.).

Analysis calculated for $C_{13}H_{12}ClNO_5S$: C, 47.35; H, 3.67; N, 4.25; Found: C, 47.33; H, 3.67; N, 4.19.

EXAMPLE 2

2-Butylamino-4-chloro-5-methylsulfonylbenzoic acid

A mixture of 2,4-dichloro-5-methylsulfonylbenzoic acid (6.0 g.; 0.0224 mole), butylamine (9 ml.) and ethyl cellosolve (20 ml.) is heated at reflux in a nitrogen atmosphere for 5 hours. The solvent is distilled at reduced pressure and the residue is dissolved in water (75 ml.) then treated with dilute hydrochloric acid which causes the product to precipitate. After recrystallization from butyl chloride there is collected 2.3 g. (34% yield) of 2-butylamino-4-chloro-5-methylsulfonylbenzoic acid, m.p. 187°–9° C.

Analysis calculated for $C_{12}H_{16}ClNO_4S$: C, 47.13; H, 5.27; N, 4.58; Found: C, 47.45; H, 5.45; N, 4.63.

EXAMPLE 3

2-Benzylamino-4-chloro-5-methylsulfonylbenzoic acid

This product is prepared following substantially the same procedure described in Example 1, Step C, using the following substances:

2,4-dichloro-5-methylsulfonylbenzoic acid — 11.0 g. (0.4 mole)

benzylamine — 22 ml.

The above procedure gives 8.0 g. (59%) of 2-benzylamino-4 -chloro-5-methylsulfonylbenzoic acid which after recrystallization from ethanol-water melts at 179° C. (corr.).

Analysis calculated for $C_{15}H_{14}ClNO_4S$: C, 53.02; H, 4.15; N, 4.12; Found: C, 52.72; H, 4.05; N, 4.25.

Alternate Preparation of Example 3 Product

EXAMPLE 4

Step A: Preparation of 4-chloro-5-methylsulfonylanthranilic acid

A solution of 2,4-dichloro-5-methylsulfonylbenzoic acid (Example 1, Step B) (60 g.; 0.267 mole) in aqueous ammonia (28%, 900 ml.) is heated in an autoclave at 180° C. for 12 hours. The cooled reaction mixture is poured into ice (3 kg.) and concentrated hydrochloric acid (1.3 liters) which causes the product to precipitate 42 g. (64% yield) of 4-chloro-5-methylsulfonylanthranilic acid, m.p. 286.5°–288.5° C. after recrystallization from acetic acid.

Analysis calculated for $C_8H_8ClNO_4S$: C, 38.48; H, 3.23; N, 5.61; Found: C, 38.64; H, 3.47; N, 5.64.

Step B: Preparation of 2-benzylamino-4-chloro-5-methylsulfonylbenzoic acid

A solution of 4-chloro-5-methylsulfonylanthranilic acid (250 mg.) and benzyl bromide (180 mg.) in 5% aqueous sodium hydroxide is heated on a water bath at 50° C. for four hours during which time 5% aqueous sodium hydroxide is added a few drops at a time to maintain a basic reaction medium. The reaction mixture is poured into water and acidified with hydrochloric acid to give 2-benzylamino-4-chloro-5-methylsulfonylbenzoic acid, m.p. 179° C. after recrystallization from ethanol and water.

EXAMPLE 5

2-Furfurylamino-4-methyl-5-methylsulfonylbenzoic acid

This product is prepared by replacing the 2,4-dichloro-5-chlorosulfonylbenzoic acid employed in Example 1, Step A, by an equimolecular proportion of 4-methyl-5-chlorosulfonylanthranilic acid and then following substantially the same procedure described in Example 1, Steps A and B, there is obtained 4-methyl-5-methylsulfonylanthranilic acid employed in the following step without purification. The compound thus obtained is combined with excess furfural and heated on a water bath at about 80° C. The water formed during the reaction is removed by azeotropic distillation with the excess furfural at about 15 mm. Hg. pressure over a one hour period. The 2-furfurylideneamino-4-methyl-5-methylsulfonylbenzoic acid formed is stirred while cooling in acetic acid while a mixture of trimethylamine-borane complex in acetic acid is added over a 10 minute period. The reaction mixture then is heated on the steam bath for 5–10 minutes, then quenched in ice water to give 2-furfurylamino-4-methyl-5-methylsulfonylbenzoic acid.

EXAMPLE 6

2-Furfurylamino-4-trifluoromethyl-5-methylsulfonylbenzoic acid

By replacing the 4-methyl-5-chlorosulfonylanthranilic acid employed in Example 5 by an equivalent quantity of 4-trifluoromethyl-5-chlorosulfonylanthranilic acid and then following the procedures of Example 5, there is obtained 2-furfurylamino-4-trifluoromethyl-5-methylsulfonylbenzoic acid.

EXAMPLE 7

2-Furfurylamino-4-chloro-5-ethylsulfonylbenzoic acid

Step A: Preparation of 2,4-dichloro-5-carboxybenzenesulfinic acid

This compound is prepared following substantially the same procedure described in Example 1, Step A, using the following substances:

| | |
|---|---|
| 2,4-dichloro-4-chlorosulfonylbenzoic acid | 145 g. (0.5 mole) |
| 10N sodium hydroxide | 145 ml. |
| sodium sulfite | 189 g. (1.5 mole) |
| water | 0.5 liter | and is used in Step B without further purification.

Step B: Preparation of 2,4-dichloro-5-ethylsulfonylbenzoic acid

This compound is prepared following substantially the same procedure described in Example 1, Step B, using the following substances:

| | |
|---|---|
| product of Step A | |
| ethanol | 250 ml. |
| water | 250 ml. |
| 10N sodium hydroxide | to pH 9 |
| ethyl bromide | 140 ml. |
| ethyl iodide | 10 ml. |

The above procedure gives 28 g. of 2,4-dichloro-5-ethylsulfonylbenzoic acid which after recrystallization from ethanol-water melts at 165°–7° C. (corr.).

Analysis calculated for $C_9H_8Cl_2O_4S$: C, 38.18; H, 2.85; Cl, 25.04; Found: C, 38.47; H, 2.87; Cl, 25.00.

Step C: Preparation of 2-furfurylamino-4-chloro-5-ethylsulfonylbenzoic acid

The product is prepared following substantially the same procedure described in Example 1, Step C, using the following substances:

2,4-dichloro-5-ethanesulfonylbenzoic acid — 5 g. (0.0176 mole)

furfurylamine — 10 ml.

The above procedure gives 4.5 g. (75%) of 2-furfurylamino-4-chloro-5-ethylsulfonylbenzoic acid which after recrystallization from nitromethane melts at 196° C. (corr.).

Analysis calculated for $C_{14}H_{14}ClNO_3S$: C, 48.91; H, 4.10; N, 4.07; Found: C, 49.02; H, 4.29; N, 4.11.

EXAMPLE 8

2-Furfurylamino-4-chloro-5-isopropylsulfonylbenzoic acid

Step A: Preparation of 2,4-dichloro-5-carboxybenzenesulfinic acid

This compound is prepared following substantially the same procedure described in Example 1, Step A, using the following substances:

| | |
|---|---|
| sodium sulfite | 75 g. |
| water | 200 ml. |
| 2,4-dichloro-4-chlorosulfonylbenzoic acid | 58 g. |
| 10N sodium hydroxide | 50 ml. | and is used in step B without further purification.

Step B: Preparation of 2,4-dichloro-5-isopropylsulfonylbenzoic acid

This compound is prepared following substantially the same procedure described in Example 1, Step B, using the following substances:

| | |
|---|---|
| product of Step A | |
| 2-propanol | 100 ml. |
| water | 60 ml. |
| 10N sodium hydroxide | to pH 9 |
| 2-iodopropane | 124 g. |

The above procedure gives 19 g. of 2,4-dichloro-5-isopropylsulfonylbenzoic acid which after recrysallization from nitromethane melts at 211°–213° C. (corr.).

Analysis calculated for $C_{10}H_{10}Cl_2O_4S$: C, 40.42; H, 3.39; Cl, 23.86; Found: C, 40.33; H, 3.33; Cl, 23.72.

Step C: Preparation of 2-furfurylamino-4-chloro-5-isopropylsulfonylbenzoic acid

This product is prepared following substantially the same procedure described in Example 1, Step C, using the following substances:

2,4-dichloro-5-isopropylsulfonylbenzoic acid — 5.0 g. (0.0168 mole)

furfurylamine — 10 ml.

The above procedure gives 3.2 g. (54%) of 2-furfurylamino-4-chloro-5-isopropylsulfonylbenzoic acid which after recrystallization from nitromethane melts at 192°–3° C. (corr.).

Analysis calculated for $C_{15}H_{16}ClNO_5S$: C, 50.35; H, 4.51 N, 3.91; Found: C, 50.18; H, 4.45; N, 4.02.

EXAMPLE 9

2-(3-Trifluoromethylanilino)-4-chloro-5-methylsulfonylbenzoic acid

This product is prepared following substantially the same procedure described in Example 1, Step C, using the following substances:

2,4-dichloro-5-methylsulfonylbenzoic acid — 2.0 g.

n-trifluoromethylaniline — 10 ml.

The above procedure gives 1.2 g. or 2-(3-trifluoromethylanilino)-4-chloro-5-methylsulfonylbenzoic acid which after recrystallization from toluene melts at 247°–485° C. (corr.).

Analysis calculated for $C_{15}H_{11}ClF_3NO_4S$: C, 45.75; H, 2.82; N, 3.56; Found: C, 46.11; H, 2.93; N, 3.48.

The products identified in Table I can be prepared by the procedure described in Example 1, Step C, by replacing the furfurylamine by an equivalent quantity of the amine identified in the following table.

TABLE I

| Example No. | R¹ |
|---|---|
| 10 |  |
| 11 |  |
| 12 | —CH₂CH₂OH |
| 13 |  |
| 14 | 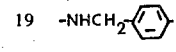 |
| 15 | —NH₂ |
| 16 | —NH(CH₂)₂CH₃ |
| 17 | —N(CH₃)₂ |

EXAMPLE 18

2-(1-Naphthylmethyl)amino-4-chloro-5-methylsulfonylbenzoic acid 2,4-Dichloro-5-methylsulfonylbenzoic acid (5.4 g.; 0.02 mole), 1-aminomethylnaphthylene (3.2 g.; 0.02 mole), and triethylamine (4 ml.) are added to diglyme (50 ml.). The resulting solution is refluxed with stirring for 4 hours. The reaction solution is cooled to room temperature and is slowly added to a solution of concentrated hydrochloric acid (10 ml.) in water (150 ml.) The aqueous layer is decanted from the viscous oil that separates. This viscous oil is dissolved in ethanol (25 ml.) and the resulting solution is poured into water. The tan colored solid which precipitates is collected and dried, yield 5.5 g. (70%). After several recrystallizations from acetonitrile, the 2-(1-naphthylmethyl)amino-4-chloro-5-methylsulfonylbenzoic acid melts at 242°–246° C. (dec. with eff.).

Analysis calculated for $C_{19}H_{16}ClNO_4S$: C, 58.53; H, 4.14; N, 3.59; Found: C, 58.49; H, 4.32; N, 3.72.

Additional compounds made following substantially the same procedure described in Example 18 are identified in Table II. Equimolecular quantities of 2,4-dichloro-5-methylsulfonylbenzoic acid, R¹NH₂ and triethylamine are employed and diglyme is used as solvent.

TABLE II

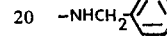

| Ex. No. | R¹ | Yield % | m.p. °C. | ANALYSIS* C | H | N |
|---|---|---|---|---|---|---|
| 19 |  | 27 | 193 | C: 48.14<br>F: 48.15 | 3.50<br>3.60 | 3.74<br>3.69 |
| 20 |  | 21 | 249.5 | C: 47.12<br>F: 46.90 | 3.21<br>3.24 | 3.43<br>3.44 |
| 21 | 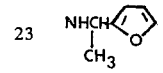 | 46 | 232.5 | C: 47.12<br>F: 47.42 | 3.21<br>3.35 | 3.43<br>3.39 |
| 22 |  | 25 | 219 | C: 50.35<br>F: 50.69 | 3.66<br>3.94 | 3.91<br>3.90 |
| 23 | 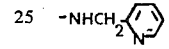 | | 174 | C: 48.91<br>F: 48.93 | 4.10<br>4.50 | 4.07<br>4.02 |
| 24 | NHCH₂-(H)-CH₂OH | 43 | 252.5–253.5 | C: 51.13<br>F: 51.20 | 5.90<br>5.88 | 3.73<br>3.65 |
| 25 |  | 63 | 219–223.5 | C: 49.34<br>F: 49.31 | 3.84<br>3.95 | 8.22<br>8.26 |
| 26 | NHCH₂-⟨N⟩ | 51 | 264–267 | C: 49.34<br>F: 49.32 | 3.84<br>3.97 | 8.22<br>8.29 |

*C = Calculated
F = Found

The following compounds also can be prepared by the process described in Example 18 by replacing the 1-aminomethylnaphthylene by an equimolecular quantity of the amine identified in Table III.

TABLE III $$Cl-\underset{CH_3O_2S-}{\bigcirc}-Cl \quad +R'NH_2 \quad \xrightarrow[\text{diglyme}]{(C_2H_5)_3N} \quad Cl-\underset{CH_3O_2S-}{\bigcirc}-NHR'$$

| Example No. | R' |
|---|---|
| 27 | $-CH_2-\underset{S}{\bigcirc}$ |
| 28 | $-CH_2-\underset{O}{\bigcirc H}$ |
| 29 | $-CH_2CF_3$ |
| 30 | $-CH_2CH_2CF_3$ |
| 31 | $-CH_2CH_2N(CH_3)_2$ |

EXAMPLE 32

2-(5-Carboxyfurfurylamino)-4-chloro-5-methylsulfonylbenzoic acid

A mixture of 2,4-dichloro-5-methylsulfonylbenzoic acid (3.50 g.; 0.013 mole), 5-aminomethyl-2-furancarboxylic acid hydrochloride (4.83 g.; 0.027 mole), triethylamine (11.5 ml.), and glyme (25 ml.) is heated to 140°–150° C. for 24 hours. Solid sodium bicarbonate (5.0 g.) is added and refluxing is continued for another 24 hours. The mixture is poured into water (150 ml.) and acidified by the addition of 6N hydrochloric acid. The tan solid is collected, washed with water, and dried, 1.20 g., m.p. 269°–272° C. Recrystallization from acetonitrile gives 2-(5-carboxyfurfurylamino)-4-chloro-5-methylsulfonylbenzoic acid, m.p. 263.5°–265.5° C. (dec.).

Analysis calculated for $C_{14}H_{12}ClNO_7S$: C, 44.98; H, 3.24; N, 3,75; Found: C, 45.29; H, 3.30; N, 3.82.

EXAMPLE 33

2-Furfurylamino-4-chloro-5-methylsulfinylbenzoic acid

Step A: Preparation of 2,4-dichloro-5-mercaptobenzoic acid

A stirred solution of 2,4-dichloro-5-chlorosulfonylbenzoic acid (43 g.; 0.15 mole) in acetic acid (560 ml.) is warmed to 75° C. in a steam bath and treated in one portion with a solution of stannous chloride dihydrate (168 g.; 0.75 mole) in concentrated hydrochloric acid (149 ml.). The reaction is heated at 75° C. for one-half hour then poured into a cold solution of hydrochloric acid (270 ml.) in water (2.2 liters). The product, 2,4-dichloro-5-mercaptobenzoic acid, separates (30 g.; 90% yield), m.p. 254°–5° C. after recrystallization from acetic acid.

Analysis calculated for $C_7H_4Cl_2O_2S$: C, 37.69; H, 1.81; Cl, 31.79; Found: C, 37.88; H, 1.78; Cl, 31.61.

Step B: Preparation of 2,4-dichloro-5-methylthiobenzoic acid

A stirred solution of 2,4-dichloro-5-mercaptobenzoic acid (30 g.; 0.135 mole) in 50% aqueous ethanol (500 ml.) and sufficient 10N sodium hydroxide to attain a pH of 9 is heated to reflux and treated dropwise with dimethyl sulfate (26 g.; 0.206 mole) during a two hour period. The pH is maintained at 9 during the addition. The reaction mixture then is cooled, diluted with water (1 liter) and acidified with dilute hydrochloric acid, yielding 30 g.; (94%) of 2,4-dichloro-5-methylthiobenzoic acid, m.p. 187° C. after recrystallization from nitromethane.

Analysis calculated for $C_8H_6Cl_2O_2S$: C, 40.52; H, 2.55; Cl, 29.91; Found: C, 40.50; H, 2.70; Cl, 30.11.

Step C: Preparation of 2,4-dichloro-5-methylsulfinylbenzoic acid

To a solution of sodium meta-periodate (8.96 g; 0.042 mole) in water (100 ml.) cooled in ice water to 20° C. is added a solution of 2,4-dichloro-4-methylthiobenzoic acid (9.48 g.; 0.04 mole) in water (100 ml.). The reaction mixture is refrigerated for 12 hours, filtered from precipitated sodium iodate and acidified with dilute hydrochloric acid. The 2,4-dichloro-5-methylsulfinylbenzoic acid which separates (8.5 g.; 85%) melts at 200°–201° C. after recrystallization from nitromethane.

Analysis calculated for $C_8H_6Cl_2O_3S$: C, 37.96; H, 2.39; Cl, 28.02; Found: C, 38.35; H, 2.64; Cl, 28.11.

Step D: Preparation of 2-furfurylamino-4-chloro-5-methylsulfinylbenzoic acid

This product is prepared following substantially the same procedure described in Example 1, Step C, using the following substances:

2,4-dichloro-5-methylsulfinylbenzoic acid—4.0 g. (0.0158 mole)

furfurylamine — 10 ml.

The above procedure gives 1.0 g. (20%) of 2-furfurylamino-4-chloro-5-methylsulfinylbenzoic acid which after recrystallization from nitromethane melts at 185°–6° C. (corr.).

Analysis calculated for $C_{13}H_{12}ClNO_4S$: C, 49.76; H, 3.85; N, 4.46; Found: C, 49.71; H, 3.97; N, 4.44.

EXAMPLE 34

2-Benzylamino-4-chloro-5-methylsulfinylbenzoic acid

The above product is prepared following substantially the same procedure described in Example 1, Step C, using the following substances 2,4-dichloro-5-methylsulfinylbenzoic acid (Example 33, Step C) — 10.0 g. (0.04 mole)

benzylamine —25 ml.

The above procedure gives 9.0 g. (72%) of 2-benzylamino-4-chloro-5-methylsulfinylbenzoic acid which after recrystallization from nitromethane melts at 218° C. (corr.).

Analysis calculated for $C_{15}H_{14}ClNO_3S$: C, 55.64; H, 4.36; N, 4.33; Found: C, 55.57; H, 4.34; N, 4.38.

EXAMPLE 35

2-Furfurylamino-4-chloro-5-trifluoromethylsulfonylbenzoic acid

Step A: Preparation of 2,4-dichloro-5-methylthiobenzoyl chloride

A solution of 2,4-dichloro-5-methylthiobenzoic acid (63 g.; 0.28 mole) in thionyl chloride (240 ml.) is refluxed for six hours and then the excess thionyl chloride is distilled at reduced pressure. The resulting oil is dissolved in hexane (800 ml.) and cooled to give 50 g. (70%) of 2,4-dichloro-5-methylthiobenzoyl chloride, m.p. 94°–95° C.

Analysis calculated for $C_8H_5Cl_3OS$:

C, 37.60; H, 1.97; Cl, 41.62; Found: C, 37.69; H, 2.07; Cl, 41.6.

Step B: Preparation of 2,4-dichloro-5-trichloromethylthiobenzoyl chloride

A solution of 2,4-dichloro-5-methylthiobenzoyl chloride (25 g.; 0.097 mole) in chloroform (1.30 ml.) is cooled in ice water to 20° C. and irradiated with a 200 watt bulb while a slow stream of chlorine is bubbled into the reaction mixture for four hours. The reaction mixture is stirred at 25° C. for 18 hours; then the solvent is removed by distillation at reduced pressure. The 2,4-dichloro-5-trichloromethylthiobenzoyl chloride which remains (14.0 g.; 40%) melts at 79°–81° C. after recrystallization from hexane.

Analysis calculated for $C_8H_2Cl_6O$: C, 26.77; H, 0.56; Cl, 59.27; Found: C, 27.08; H, 0.62; CL, 59.57.

Step C: Preparation of 2,4-dichloro-5-trifluoromethylthiobenzoic acid

A 200 ml. flask is charged with a mixture of 2,4-dichloro-5-trichloromethylthiobenzoyl chloride (14 g.; 0.039 mole) and antimony trifluoride (15 g.; 0.085 mole). The flask is heated with a flame until a frothing reaction commences then it is heated intermittantly for five minutes and poured into ice water (200 ml.) containing hydrochloric acid (50 ml.). The product is extracted into ether (150 ml.) and wahed with 3N hydrochloric acid (3 × 50 ml.). The ether is removed by distillation at reduced pressure and the residual oil is treated with water (100 ml.), ethanol (100 ml.) and 10N sodium hydroxide (20 ml.). The mixture is refluxed for 2 hours, cooled and acidified with hydrochloric acid to give 10.0 g. (88%) of 2,4-dichloro-5-trifluoromethylthiobenzoic acid, m.p. 112°–114° C. after recrystallization from acetic acid-water.

Analysis calculated for $C_8H_3F_3Cl_2O_2S$: C, 33.01; H, 1.04; Cl, 24.36; Found: C, 33.14; H, 1.13; Cl, 24.41.

Step D: Preparation of 2,4-dichloro-5-trifluoromethyl sulfonylbenzoic acid

A solution of 2,4-dichloro-5-trifluoromethylthiobenzoic acid (2.7 g.; 0.0093 mole) in acetic acid (10 ml.) is added dropwise to a stirred solution of chromium trioxide (5 g.) in acetic acid at such a rate that the temperature does not exceed 50° C. Thereafter, the reaction mixture is refluxed for 2 hours, cooled and poured into water (300 ml.). The 2,4-dichloro-5-trifluoromethyl sulfonylbenzoic acid which separates (1.0 g.; 33%) melts at 192°–3° C. after recrystallization from butyl chloride.

Analysis calculated for $C_8H_3Cl_2F_3O_4S$: C, 29.74; H, 0.96; F, 17.64; Found: C, 29.78; H, 0.96; F, 17.51.

Step E: Preparation of 2-furfurylamino-4-chloro-5-trifluoromethylsulfonylbenzoic acid A mixture of 2,4-dichloro-5-trifluoromethylsulfonylbenzoic acid (1.2 g.; 0.0037 mole) and furfurylamine (4 ml.) is heated on a steam bath for four hours then poured into water (30 ml.) containing hydrochloric acid (6 ml.). The 2-furfurylamino-4-chloro-5-trifluoromethylsulfonylbenzoic acid which separates (1.1 g.; 77%) melts at 211° C. (dec.) after recrystallization from ethanol-water mixture.

Analysis calculated for $C_{13}H_9ClF_3NO_5S$: C, 40.69; H, 2.36; N, 3.65; Found: C, 41.06; H, 2.50; N, 4.15.

EXAMPLE 36

2-Furfurylamino-4-chloro-5-trifluoromethylsulfinylbenzoic acid

Step A: Preparation of 2,4-dichloro-5-trifluoromethylsulfinylbenzoic acid

To a refluxing solution of 2,4-dichloro-5-trifluoromethylthiobenzoic acid (Example 35, Step C) (9.0 g.; 0.031 mole) in acetic acid (60 ml.) is added 20% aqueous hydrogen peroxide (17 ml.) dropwise during ½ hour. Refluxing is continued ½ hour then the reaction mixture is diluted with water (125 ml.). The 2,4-dichloro-5-trifluoromethylsulfinylbenzoic acid which separates (8.0 g.; 35%) melts at 176°–178° C. after recrystallization from butyl chloride.

Analysis calculated for $C_8H_3Cl_2F_3O_3S$: C, 31.29; H, 0.98; Found: C, 31.23; H, 1.03.

Step B: Preparation of 2-furfurylamino-4-chloro-5-trifluoromethylsulfinylbenzoic acid This product is prepared following substantially the same procedure described in Example 35, Step E, using the following substances:

2,4-dicholoro-5-trifluoromethylsulfinyl-benzoic acid — 5.5 g. (0.018 mole)

furfurylamine — 13 ml.

The above procedure gives 4.5 g. (68%) of 2-furfurylamino-4-chloro-5-trifluoromethylsulfinylbenzoic acid which after recrystallization from ethanol-water melts at 190°–191° C.

Analysis calculated for $C_{13}H_9ClF_3NO_4S$: C, 42.46; H, 2.47; N, 3.81; Found: C, 42.33; H, 2.43; N, 3.77.

EXAMPLE 37

N-Amidino-2-furfurylamino-4-chloro-5-methylsulfonylbenzamide

Step A: Preparation of N-tert-butyl-3-(2-furfurylamino-4-chloro-5-methylsulfonylbenzoyloxy)-crotonamide N-tert-butyl-5-methylisoxazolium perchlorate (120 g.; 0.005 mole) is added to a solution of 2-furfurylamino-4-chloro-5-methylsulfonylbenzoic acid (1.65 g.; 0.005 mole) and triethylamine (0.7 ml.) in dimethylformamide (15 ml.). The resulting solution is allowed to stir at room temperature for 2 hours, and then diluted with $H_2O$ (75 ml.). The white solid which precipitates is collected and dried, yield 2.4 g. (crude), m.p. 140°–145° C. Recrystallization from butyl chloride yields N-tert-butyl-3-(2-furfurylamino-4-chloro-5-methylsulfonylbenzoyloxy)crotonamide, m.p. 148.5°–150° C. (dec. with eff.).

Analysis calculated for $C_{21}H_{25}ClN_2O_6S$: C, 53.78; H, 5.37; N, 5.98; Found: C, 54.16; H, 5.54; H, 6.03.

Step B: Preparation of N-amidino-2-furfurylamino-4-chloro-5-methylsulfonylbenzamide Sodium (0.46 g.; 0.02 mole) is dissolved in absolute methanol (50 ml.), guanidine hydrochloride (1.91 g.; 0.02 mole) is added and this mixture is allowed to stir at room temperature for one hour. The methanol is removed under reduced pressure, and the residue is taken up in tetrahydrofuran. N-tert-butyl-3-(2-furfurylamino-4-chloro-5-methylsulfonylbenzoyloxy) crotonamide is added and the mixture is allowed to stir at ambient temperature for another three hours. The tetrahydrofuran is removed under reduced pressure, and the residue is dissolved in water (50 ml.). The light yellow solid which forms is collected and dried, 4.1 g., m.p. 96°–102° C. (unclear). Several recrystallizations from absolute ethanol yields N-amidino-2-furfurylamino-4-chloro-5-methylsulfonylbenzamide in the form of light yellow needles, m.p. 206°–208° C.

Analysis calculated for $C_{14}H_{15}ClN_4O_4S$: C, 45.34; H, 4.08; N, 15.11; Found: C, 45.28; H, 4.08; N, 15.01.

EXAMPLE 38

2-Furfurylamino-4-chloro-5-methylsulfonylbenzoic acid 2,2-dimethylhydrazide

N-tert-butyl-3-(2-furfurylamino-4-chloro-5-methylsulfonylbenzoyloxy)crotonamide (4.69 g.; 0.01 mole) and unsymmetrical-dimethylhydrazine (1.20 g.; 0.02 mole) are added to acetonitrile. The reaction mixture is refluxed with stirring for 24 hours. Additional unsymmetrical-dimethylhyrazine (1.20 g.; 0.02 mole) is added, and refluxing is continued for an additional 24 hours. The acetonitrile is removed under reduced pressure, and the dark residue is triturated with isopropyl alcohol. The tan colored solid which crystallizes is collected and dried, yield 2.4 g. (64%), m.p. 90°–104° C. Several recrystallizations from butyl chloride followed by a recrystallization from benzene yields 2-furfurylamino-4-chloro-5-methylsulfonylbenzoic acid 2,2-dimethylhydrazide in the form of a white solid, m.p. 169.5°–171° C.

Analysis calculated for $C_{15}H_{18}ClN_3O_4S$: C, 48.45; H, 4.88; N, 11.30; Found: C, 48.46; H, 4.90; N, 11.15.

EXAMPLE 39

N-(2-dimethylaminoethyl)-2-furfurylamino-4-chloro-5-methylsulfonylbenzamide

N-tert-butyl-3-(2-furfurylamino-4-chloro-5-methylsulfonylbenzoyloxy)crotonamide (4.69 g.; 0.01 mole) and 1,1-dimethylethylenediamine (1.76 g.; 0.02 mole) are added to acetonitrile (100 ml.). The resulting solution is stirred at room temperature for four hours. The acetonitrile is removed under reduced pressure, and the residue is triturated with hexane. The white solid which crystallizes is collected, yield 4.4 g. Recrystallization from butyl chloride gives N-(2-dimethylaminoethyl)-2-furfurylamino-4-chloro-5-methylsulfonylbenzamide, m.p. 102.5°–105° C.

Analysis calculated for $C_{17}H_{22}ClN_3O_4S$: C, 51.06; H, 5.55; N, 10.51; Found: C, 51.38; H, 5.60; N, 10.47.

EXAMPLE 40

N-(2-morpholinoethyl)-2-furfurylamino-4-chloro-5-methylsulfonylbenzamide

N-tert-butyl-3-(2-furfurylamino-4-chloro-5-methylsulfonylbenzoyloxy)crotonamide (4.00 g.; 0.0085 mole) and N-(2-aminoethyl)morpholine (2.21 g.; 0.017 mole) are added to acetonitrile (100 ml.). The resulting solution is stirred at room temperature for 24 hours. The acetonitrile is removed under reduced pressure, and the residue is triturated with butyl chloride to give N-(2-morpholinoethyl)-2-furfurylamino-4-chloro-5-methylsulfonylbenzamide which after drying yields 2.7 g. (72%), m.p. 127°–130° C. Several recrystallizations from butyl chloride yields product with m.p. 132°–134° C.

Analysis calculated for $C_{19}H_{24}ClN_3O_5S$: C, 51.64; H, 5.47; N, 9.51; Found: C, 51.41; H, 5.46; N, 9.34.

EXAMPLE 41

2-Furfurylamino-4-chloro-5-methylsulfonylbenzamide

By replacing the unsymmetrical-dimethylhydrazine employed in Example 38 by liquid ammonia in a closed system but following substantially the same procedure described in Example 38 there is obtained 2-furfurylamino-4-chloro-5-methylsulfonylbenzamide.

EXAMPLE 42

Ethyl 2-furfurylamino-4-chloro-5-methylsulfonylbenzoate

Following the procedure described in Example 40, but replacing the N-(2-aminoethyl)morpholine by sodium ethoxide and the acetonitrile with ethanol there is obtained ethyl 2-furfurylamino-4-chloro-5-methylsulfonylbenzoate.

EXAMPLE 43

2-Diethylaminoethyl 2-furfurylamino-4-chloro-5-methylsulfonylbenzoate

By replacing the N-(2-aminoethyl)morpholine employed in Example 40 by an equivalent quantity of sodium 2-diethylaminoethoxide and the acetonitrile by 2-diethylaminoethanol and then following substantially the same procedure described in Example 40, there is obtained 2-diethylaminoethyl 2-furfurylamino-4-chloro-5-methylsulfonylbenzoate.

Additional products prepared by the process described in Example 40 employing the $HNR^4R^5$ identified in the following table are identified in Table IV:

TABLE IV

| Example No. | —$NR^4R^5$ |
|---|---|
| 44 | —$NHNH_2$ |
| 45 | —$NHC_2H_5$ |
| 46 | —$N(C_3H_7)_2$ |
| 47 | -N(H)— (piperidinyl) |
| 48 | -N(H)— |
| 49 | -N(H)— |
| 50 | -NHN(H)-CH_3 |

EXAMPLE 51

2-Furfurylamino-4-chloro-5-benzylsulfinylbenzoic acid

Step A: Preparation of 2,4-dichloro-5-benzylthiobenzoic acid

This compound is prepared following substantially the same procedure described in Example 33, Step B, using the following substances:

2,4-dichloro-5-mercaptobenzoic acid — 22.3 g. (0.1 mole)
benzyl chloride — 25 ml.
ethanol — 100 ml.
water — 60 ml.
10N sodium hydroxide — to pH 9

The above procedure gives 20 g. (64%) of 2,4-dichloro-5-benzylthiobenzoic acid which after recrystallization from nitromethane melts at 152°–3° C. (corr.)

Analysis calculated for $C_{14}H_{10}Cl_2O_2S$: C, 53.69; H, 3.22; Found: C, 54.10; H, 3.30.

Step B: Preparation of 2,4-dichloro-5-benzylsulfinylbenzoic acid

A stirred solution of 2,4-dichloro-5-benzylthiobenzoic acid (2.6 g.; 0.0083 mole) in acetic acid (50 ml.) is warmed to 60° C. on a water bath. A 30% solution of hydrogen peroxide (2.5 ml.) is added and the reaction mixture is warmed at 50°–60° C. for 2 hours then poured into water (200 ml.) containing concentrated hydrochloric acid (15 ml.). The product, 2,4-dichloro-5-benzylsulfinylbenzoic acid, which separates (2.7 g.; 98%) melts at 192.5° C. after recrystallization from nitromethane.

Analysis calculated for $C_{14}H_{10}Cl_2O_3S$: C, 51.08; H, 3.06; Cl, 21.54; Found: C, 51.45; H, 3.32; Cl, 21.60.

Step C: Preparation of 2-furfurylamino-4-chloro-5-benzylsulfinylbenzoic acid

This product is prepared following substantially the same procedure described in Example 1, Step C, using the following substances:

2,4-dichloro-5-benzylsulfinylbenzoic acid — 2.1 g. (0.0064 mole)

furfurylamine — 5 ml.

The above procedure gives 0.6 g. (24%) of 2-furfurylamino-4-chloro-5-benzylsulfinylbenzoic acid which after recrystallization fron nitromethane melts at 189.5° C. (corr.).

Analysis calculated for $C_{19}H_{16}ClNO_5S$: C, 58.54; H, 4.13; N, 3.59; Found: C, 58.60; H, 4.32; N, 3.51.

EXAMPLE 52

2-Furfurylamino-4-chloro-5-(4-chlorobenzylsulfinyl)-benzoic acid

By replacing the benzyl chloride employed in Example 51, Step A, by an equivalent quantity of p-chlorobenzyl chloride, and then following the procedures described in Example 51, Steps A through C, there is obtained 2-furfurylamino-4-chloro-5-(4-chlorobenzylsulfinyl)benzoic acid.

EXAMPLE 53

2-Furfurylamino-4-chloro-5-(4-ethylbenzylsulfinyl)-benzoic acid

By replacing the benzyl chloride employed in Example 51, Step A, by an equivalent quantity of p-ethylbenzyl chloride, and then following the procedures described Example 51, Steps A through C, there is obtained 2-furfurylamino-4-chloro-5-(4-ethylbenzylsulfinyl)benzoic acid.

EXAMPLE 54

2-Furfurylamino-4-chloro-5-(4-ethoxybenzylsulfinyl)-benzoic acid

By replacing the benzyl chloride employed in Example 51, Step A, by an equivalent quantity of p-ethoxybenzyl chloride, and then following the procedures described in Example 51, Steps A through C, there is obtained 2-furfurylamino-4-chloro-5-(4-ethoxybenzylsulfinyl)benzoic acid.

EXAMPLE 55

3-Furfurylamino-4-chloro-5-methylsulfonylbenzoic acid

Step A: Preparation of 3-methylsulfonyl-4-chlorobenzoic acid

A solution of sodium sulfite (55 g.; 0.435 mole) in water (150 ml.) is cooled to 20° C. and treated during a 30-minute period with 3-chlorosulfonyl-4-chlorobenzoic acid (37 g.; 0.145 mole) at such a rate that the temperature of the reaction mixture does not exceed 25° C. The reaction mixture is stirred at 25° C. for 3 hours, then acidified with concentrated hydrochloric acid (63 ml.). The sulfinic acid which separates is removed by filtration, and washed with cold water (50 ml.). Then the solid is placed in a flask with water (42 ml.), methanol (75 ml.), sufficient 10N sodium hydroxide to attain pH of 9 and, finally, methyl iodide (34 ml.) is added. The reaction mixture is refluxed for 20 hours while 10N sodium hydroxide is added in small portions to maintain pH of 9. The methanol is removed by distillation at reduced pressure and the reaction residual material is acidified to yield 25 g. (73%) of 3-methylsulfonyl-4-chlorobenzoic acid which melts at 227.5° C. after recrystallization from ethanol.

Analysis calculated for $C_8H_7ClO_4S$: C, 40.95; H, 3.00; Cl, 15.11; Found: C, 40.99; H, 2.98; Cl, 15.16.

Step B: Preparation of 3-methylsulfonyl-4-chloro-5-nitrobenzoic acid

To a stirred mixture of concentrated sulfuric acid (75 ml.) and concentrated nitric acid (48 ml.), cooled to 15° C., is added a solution of 3-methylsulfonyl-4-chlorobenzoic acid (31.5 g.; 0.134 mole) in concentrated sulfuric acid (185 ml.). The reaction mixture is heated on a steam bath for 2½ hours then poured into ice. There is collected 34 g. (91%) of 3-methylsulfonyl-4-chloro-5-nitrobenzoic acid, m.p. 197° C. after recrystallization from ethanol.

Analysis calculated for $C_8H_6ClNO_6S$: C, 34.36; H, 2.16; N, 5.00; Found: C, 34.39; H, 2.24; N, 5.02.

Step C: Preparation of 3-methylsulfonyl-4-chloro-5-aminobenzoic acid

A vigorously stirred mixture of iron powder (9.2 g.), ammonium chloride (880 mg.) water (27 ml.) and concentrated hydrochloric acid (0.1 ml.) is heated on a steam bath while 3-methylsulfonyl-4-chloro-5-nitrobenzoic acid (7.8 g.) is added in small portions during a one hour period. The reaction mixture is heated on a steam bath for 18 hours, cooled and filtered. The filter cake is suspended in water (75 ml.), basified with 10N sodium hydroxide, warmed to 50° C. and filtered. Acidification of the filtrate with hydrochloric acid gives pure 3-methylsulfonyl-4-chloro-5-aminobenzoic acid (4.3 g.; 62%) which melts at 277.5° C.

Analysis calculated for $C_8H_8ClNO_4S$: C, 38.48; H, 3.23; N, 5.61; Found: C, 38.59; H, 3.18; N, 5.57.

Step D: Preparation of 3-furfurylideneamino-4-chloro-5-methylsulfonylbenzoic acid A mixture of 3-methylsulfonyl-4-chloro-5-aminobenzoic acid (3.0 g.; 0.012 mole) and furfural (50 ml.) is heated to 70°–80° C. on a water bath. The water formed during the reaction is azeotropically distilled with the excess furfural at 15 mm Hg. pressure during a one hour period. The reaction mixture is cooled and triturated with carbon tetrachloride (100 ml.) to yield 3.6 g. (90%) of 3-furfurylideneamino-4-chloro-5-methylsulfonylbenzoic acid which melts at 221° C. and is used in Step E without further purification.

Step E: Preparation of 3-furfurylamino-4-chloro-5-methylsulfonylbenzoic acid

A stirred suspension of 3-furfurylideneamino-4-chloro-5-methylsulfonylbenzoic acid (3.6 g.) in acetic acid (50 ml.) is cooled to 20° C. and treated over a ten minute period with a solution of trimethylamineborane complex (800 mg.) in acetic acid (10 ml.). The reaction mixture is heated on a steam bath for 5 minutes then poured into ice water (250 ml.). The 3-furfurylamino-4-chloro-5-methylsulfonylbenzoic acid which separates (3.1 g., 85%) melts at 215.5°–216.5° C. after recrystallization from nitromethane.

Analysis calculated for $C_{13}H_{12}ClNO_5S$: C, 47.35; H, 3.67; N, 4.19; Found: C, 46.83; H, 3.67; N, 4.22.

EXAMPLE 56

3-Furfurylamino-4-methyl-5-methylsulfonylbenzoic acid

4-Methylbenzoic acid (0.2 mole) is added to chlorosulfonic acid (50 ml.) and heated at reflux for about one hour, cooled and poured onto ice. The product, 3-chlorosulfonyl-4-methylbenzoic acid that separates is then employed in place of the 2,4-dichloro-5-chlorosulfonylbenzoic acid in the process described in Example 1, Step A, and then following the methods described in Steps A and B of Example 1 there is obtained 3-methylsulfonyl-4-methylbenzoic acid. This compound then is substituted for the 3-methylsulfonyl-4-chlorobenzoic acid employed in Step B of Example 55 and then by following substantially the same procedures described in Example 55, Steps B through E, there is obtained 3-furfurylamino-4-methyl-5-methylsulfonylbenzoic acid.

EXAMPLE 57

3-Furfurylamino-4-chloro-5-benzylsulfonylbenzoic acid

By replacing the methyl iodide employed in Step A of Example 55 by an equivalent quantity of benzyl iodide and then following substantially the same procedures described in Steps A through E of Example 55, there is obtained 3-furfurylamino-4-chloro-5-benzylsulfonylbenzoic acid.

EXAMPLE 58

3-Benzylamino-4-chloro-5-methylsulfonyl benzoic acid

To a solution of 3-methylsulfonyl-4-chloro-5-aminobenzoic acid (1.25 g.) in 1N sodium hydroxide (5 ml.) is added benzyl bromide (1 ml.). The stirred reaction is heated at 45°–50° C. for 6 hours with the occasional addition of a few drops of 1N sodium hydroxide to maintain a pH of 9. The reaction mixture is diluted with water (50 ml.) and acidified with 1N hydrochloric acid to give 0.9 g. (53%) of 3-benzylamino-4-chloro-5-methylsulfonylbenzoic acid, m.p. 254°–256.5° C. after recrystallization from nitromethane.

Analysis calculated for $C_{15}H_{14}ClNO_4S$: C, 53.02; H, 4.15; N, 4.12; Found: C, 52.47; H, 4.13; N, 4.32.

The process of Example 55 lends itself to the preparation of the compounds of this invention of the structure

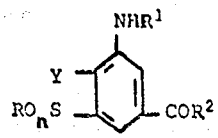

wherein $R^1$ is any one of the groups hereinbefore described. By following the procedure described in this example and replacing the alkylating or aralkylating agents by the agent identified in the following table, the products also identified in Table V are obtained.

TABLE V

![structures showing Cl/CH3O2S-substituted aminobenzoic acid + R¹ halide → N-alkylated product]

| Example No. | $R^1$ |
|---|---|
| 59 | $-CH_2CH_2CH_2CH_3$ |
| 60 | cyclopropyl (–⟨H⟩) |
| 61 | $-CH_2$–(4-chlorophenyl) |
| 62 | $-CH_2$–naphthyl |
| 63 | $-CH_2$–pyridyl |

EXAMPLE 64

N-amidino-3-furfurylamino-4-chloro-5-methylsulfonylbenzamide

By replacing the 2-furfurylamino-4-chloro-5-methylsulfonylbenzoic acid employed in Step A of Example 37 by an equivalent quantity of 3-furfurylamino-4-chloro-5-methylsulfonylbenzoic acid and then following substantially the same procedure described in Example 37, Steps A and B, there is obtained N-amidino-3-furfurylamino-4-chloro-5-methylsulfonylbenzamide.

EXAMPLE 65

3-Furfurylamino-4-chloro-5-methylsulfonylbenzoic acid 2,2-dimethylhydrazide

By replacing the crotonamide employed in Example 38 by an equivalent quantity of N-tert-butyl-3-(3-furfurylamino-4-chloro-5-methylsulfonylbenzoyloxy)-crotonamide (prepared as described in the previous example) and then following substantially the same procedure described in Example 38, there is obtained 3-furfurylamino-4-chloro-5-methylsulfonylbenzoic acid 2,2-dimethylhydrazide.

EXAMPLE 66

N-(2-dimethylaminoethyl)-3-furfurylamino-4-chloro-5-methylsulfonylbenzamide

By replacing the crotonamide employed in Example 39 by an equimolecular quantity of N-tert-butyl-3-(3-furfurylamino-4-chloro-5-methylsulfonylbenzoyloxy)-crotonamide and then following substantially the same procedure described in Example 39, there is obtain N-(2-dimethylaminoethyl)-3-furfurylamino-4-chloro-5-methylsulfonylbenzamide.

EXAMPLE 67

N-(2-morpholinoethyl)-3-furfurylamino-4-chloro-5-methylsulfonylbenzamide

By replacing the crotonamide employed in Example 40 by an equimolecular quantity of N-tert-butyl-3-(3-furfurylamino-4-chloro-5-methylsulfonylbenzoyloxy)-crotonamide and then following substantially the same procedure described in Example 40, there is obtained N-(2-morpholinoethyl)-3-furfurylamino-4-chloro-5-methylsulfonylbenzamide.

EXAMPLE 68

3-n-Butylamino-4-chloro-5-methylsulfinylbenzoic acid

Step A: Preparation of 3-Nitro-4-chloro-5-chlorosulfonylbenzoic acid

To a mixture of concentrated sulfuric acid (87 ml.) and concentrated nitric acid (16 ml., density = 1.42) is added 3-chlorosulfonyl-4-chlorobenzoic acid (11.5 g.; 0.045 mole). The reaction mixture is heated at 85°–90° C. with stirring for 20 hours then poured into ice water. The 3-nitro-4-chloro-5-chlorosulfonylbenzoic acid which separates is filtered, washed with water and dried, m.p. = 189°–90° C. (corr.); yield, 6.6 g. (50%).

Step B: Preparation of 3-Amino-4-chloro-5-mercaptobenzoic acid Hydrochloride

A solution of 3-nitro-4-chloro-5-chlorosulfonylbenzoic acid (33 g.; 0.11 mole) in acetic acid (550 ml.) is warmed to 70° C. on a water bath and treated in one portion with a solution of stannous chloride dihydrate (226 g.; 1.0 mole) in concentrated hydrochloride acid (190 ml.). The reaction is stirred at 70°–80° C. for one-half hour, chilled in ice and the tin complex which separates is filtered, rinsed with acetic acid and dissolved in water (300 ml.). The solution is treated with concentrated hydrochloric acid (150 ml.) whereupon 3-amino-4-chloro-5-mercaptobenzoic acid hydrochloride separates, m.p. = 239.5° C.; yield, 20.5 g. (77%).

Analysis calculated for $C_7H_7Cl_2NO_2S$: C, 35.01; H, 2.94; N, 5.83; Found: C, 35.43; H, 2.88; N, 5.72.

Step C: Preparation of 3-Amino-4-chloro-5-methylthiobenzoic acid

A solution of 3-amino-4-chloro-5-mercaptobenzoic acid hydrochloride (23 g.; 0.096 mole) in 50% aqueous ethanol (350 ml.) is made basic with 10N sodium hydroxide to pH = 9, and refluxed while dimethyl sulfate (14.2 ml.) is added dropwise during a one-hour period. Heating is continued for three hours and 10N sodium hydroxide is added in small portions to maintain pH 9. The reaction is cooled and acidified with hydrochloric acid to give 18 g. of 3-amino-4-chloro-5-methylthiobenzoic acid (87%) which melts at 225° C. after recrystallization from ethanol.

Analysis calculated for $C_8H_8ClNO_2S$: C, 44.14; H, 3.70; N, 6.43; Found: C, 44.37; H, 3.76; N, 6.39.

Step D: Preparation of 3-Amino-4-chloro-5-methylsulfinylbenzoic acid

To a cold solution of sodium metaperiodate (2.75 g.) in water (30 ml.) is added a solution of 3-amino-4-chloro-5-methylthiobenzoic acid (2.18 g.; 0.01 mole) in water (30 ml.) containing sufficient 10N sodium hydroxide to effect solution. The reaction mixture is refrigerated for 18 hours, filtered from precipitated sodium iodate and acidified with dilute hydrochloric acid to precipitate 3-amino-4-chloro-5-methylsulfinylbenzoic acid which melts at 261° C. (dec.)

Analysis calculated for $C_8H_8ClNO_3S$: C, 41.12; H, 3.45; N, 5.99; Found: C, 41.19; H, 3.95; N, 5.64.

Step E: Preparation of 3-n-Butylamino-4-chloro-5-methylsulfinylbenzoic acid

A solution of 3-amino-4-chloro-5-methylsulfinylbenzoic acid (4.67 g.; 0.02 mole) in n-butanol (150 ml.) containing concentrated sulfuric acid (2 ml.) is refluxed for 48 hours in a Soxhlet extractor containing type 4A molecular sieves (100 g.). The solvent is distilled at reduced pressure and the residue is treated with water (50 ml.), 10N sodium hydroxide (20 ml.) and ethanol (20 ml.) and refluxed for 1 hour to hydrolyze any butyl ester which may have formed. The reaction mixture is cooled and acidified with dilute hydrochloric acid to give 3-n-butylamino-4-chloro-5-methylsulfinylbenzoic acid which melts at 158° C. after recrystallization from ethanol and water.

Analysis calculated for $C_{12}H_{16}ClNO_3S$: C, 49.74; H, 5.56; N, 4.83; Found: C, 49.64; H, 5.74; N, 4.70.

EXAMPLE 69

3-n-Butylamino-4-methyl-5-methylsulfinylbenzoic acid

This product is prepared by replacing the 3-chlorosulfonyl-4-chlorobenzoic acid used in Step A of Example 68 by an equimolar quantity of 3-chlorosulfonyl-4-methylbenzoic acid and then following the procedures described in Steps A through E of Example 68.

EXAMPLE 70

3-Furfurylamino-4-chloro-5-isopropylsulfinylbenzoic acid

By replacing the dimethyl sulfate employed in Step C of Example 68 by an equimolar quantity of 2-iodopropane and then following substantially the same procedures described in Steps C and D of Example 68 there is obtained 3-amino-4-chloro-5-isopropylsulfinylbenzoic acid. The reaction of this compound with furfuraldehyde by the process described in Example 5 provides first 3-furfurylideneamino-4-chloro-5-isopropylsulfinylbenzoic acid then 3-furfurylamino-4-chloro-5-isopropylsulfinylbenzoic acid.

EXAMPLE 71

3-Benzylamino-4-chloro-5-(4-methylbenzylsulfinyl)-benzoic acid

By replacing the dimethyl sulfate employed in Step C of Example 68 by an equimolar quantity of p-methylbenzyl chloride and then following same the sme procedures described in Example 68, Steps C and D there is obtained 3-amino-4-chloro-5-(4-methylbenzylsulfinyl)benzoic acid. Treatment of this compound with benzyl bromide following the procedure described in Step E of Example 68 yields 3-benzylamino-4-chloro-5-(4-methylbenzylsulfinyl)benzoic acid.

EXAMPLE 72

3-Cyclopropylmethylamino-4-chloro-5-methylsulfinylbenzoic acid

This product is prepared by replacing the 4-chloro-5-methylsulfonylanthranilic acid and the benzyl bromide employed in Example 4 by equivalent quantities of 3-amino-4-chloro-5-methylsulfinylbenzoic acid and cyclopropylmethyl bromide, respectively and following substantially the same procedure described in Example 4.

EXAMPLE 73

3-Furfurylamino-4-chloro-5-methylsulfinylbenzoic acid

This product is prepared by substantially the same procedure described in Example 5 by replacing the 4-methyl-5-methylsulfonylanthranilic acid by 3-amino-4-chloro-5-methylsulfinylbenzoic acid.

EXAMPLE 74

N-Amidino-3-furfurylamino-4-chloro-5-methylsulfinylbenzoic acid

By replacing the 2-furfurylamino-4-chloro-5-methylsulfonylbenzoic acid employed in Example 37, Step A, by an equimolar quantity of 3-furfurylamino-4-chloro-5-methylsulfinylbenzoic acid and then following substantially the same procedure there described there is obtained N-tertbutyl-3-(3-furfurylamino-4-chloro-5-methylsulfinylbenzoyloxy)crotonamide which, without purification is treated with guanidine by the method described in Step B of Example 37 to yield N-amidino-3-furfurylamino-4-chloro-5-methylsulfinylbenzoic acid.

EXAMPLE 75

3-Furfurylamino-4-chloro-5-methylsulfinylbenzoic acid 2,2-diethylhydrazide

By replacing the crotonamide and the unsymmetrical-dimethylhydrazine employed in Example 38 by equimolar quantities of N-tert-butyl-3-(3-furfurylamino-4-chloro-5-methylsulfinylbenzoyloxy)-crotonamide and unsymmetrical-diethylhydrazine respectively and then following substantially the same procedure described in Example 38 there is obtained 3-furfurylamino-4-chloro-5-methylsulfinylbenzoic acid 2,2-diethylhydrazide.

EXAMPLE 76

N-(2-morpholinoethyl)-3-furfurylamino-4-chloro-5-methylsulfinylbenzamide

By replacing the crotonamide employed in Example 40 by an equimolecular quantity of N-tert-butyl-3-(3-furfurylamino-4-chloro-5-methylsulfinylbenzoyloxy)-crotonamide and then following substantially the same procedure described therein, there is obtained N-(2-morpholinoethyl)-3-furfurylamino-4-chloro-5-methylsulfinylbenzamide.

We claim:
1. An aminobenzoic acid having the structure:

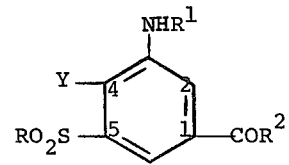

wherein Y is selected from the group consisting of (1) halo, (2) trifluoromethyl and (3) $C_{1-3}$ alkyl; R is selected from the group consisting of (1) lower alkyl; (2) halo-lower alkyl, (3) phenyl-$C_{1-3}$ alkyl, (4) (monosubstituted-phenyl)-$C_{1-3}$ alkyl wherein the substituent is selected from lower alkyl, lower alkoxy and halo; $R_1$ is selected from the group consisting of (1) phenyl-$C_{1-3}$ alkyl, (2) (monosubstitutedphenyl)-$C_{1-3}$ alkyl wherein the substituent is selected from halo, $C_{1-3}$ alkyl and $C_{1-3}$ alkoxy, (3) naphthyl-$C_{1-3}$ alkyl, (4) furyl-$C_{1-3}$ alkyl, (5) carboxyfuryl-$C_{1-3}$ alkyl, (6) thienyl-$C_{1-3}$ alkyl, (7) halo-$C_{1-3}$ alkyl, (8) hydroxy-$C_{1-3}$ alkyl, (9) di-$C_{1-3}$ alkylamino-$C_{1-3}$ alkyl, and (10) $C_{3-6}$ cycloalkyl-$C_{1-3}$ alkyl and $R_2$ is selected from the group consisting of (1) hydroxy and its pharmaceutically acceptable salts, and (2) $OR^3$ wherein $R^3$ is $C_{1-5}$ alkyl and di-$C_{1-3}$ alkylamino-$C_{1-3}$ alkyl.

2. An aminobenzoic acid as claimed in claim 1 wherein Y is halo, R is lower alkyl and $R^2$ is hydroxy.

3. An aminobenzoic acid as claimed in claim 1 wherein $R^1$ is furfuryl.

4. An aminobenzoic acid as claimed in claim 1 wherein R is lower alkyl, Y is halo, $R^1$ is furfuryl and $R^2$ is hydroxy.

5. An aminobenzoic acid as claimed in claim 1 wherein R is methyl, Y is chloro, $R^1$ is furfuryl and $R^2$ is hydroxy.

6. An aminobenzoic acid as claimed in claim 1 wherein R is methyl, Y is chloro, $R^1$ is benzyl and $R^2$ is hydroxy.

* * * * *